United States Patent [19]
Fujita et al.

[11] Patent Number: 6,106,777
[45] Date of Patent: *Aug. 22, 2000

[54] DNA ANALYZING METHOD AND DEVICE THEREFOR

[75] Inventors: Takeshi Fujita, Hatoyama-machi; Shin-ichiro Umemura, Hachioji, both of Japan

[73] Assignee: Hitachi, Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/552,496

[22] Filed: Nov. 9, 1995

[30] Foreign Application Priority Data

Nov. 9, 1994 [JP] Japan .................................. 6-274735

[51] Int. Cl.[7] .................................................. G01N 21/29
[52] U.S. Cl. .............................. 422/50; 435/6; 435/91.1; 435/287.2; 436/800; 436/807; 436/808; 536/23.1; 536/24.3; 536/24.33; 935/77; 935/78; 935/86; 935/87; 359/350; 422/82.05; 422/82.08
[58] Field of Search .......................... 435/6, 91.1, 287.2; 436/800, 807, 808; 536/23.1, 24.3, 24.33; 935/77, 78, 86, 87; 359/350; 422/50, 82.05, 82.08

[56] References Cited

U.S. PATENT DOCUMENTS

| | | | |
|---|---|---|---|
| 4,801,550 | 1/1989 | Kapuscinski et al. | 436/94 |
| 5,200,313 | 4/1993 | Carrico | 435/6 |
| 5,591,582 | 1/1997 | Bos et al. | 435/6 |

FOREIGN PATENT DOCUMENTS 7-31500 of 0000 Japan .

OTHER PUBLICATIONS

Razlutskii et al., "The effect of nucleotide substitution on DNA denaturation profiles," Nucleic Acids Research, vol. 15, No. 16, pp. 6664–6676, 1986.

Inoki et al., "In situ microspectrofluorometry of nuclear and kinetoplast DNA in Trypanosoma gambiense," Zentralbl. Bakteriol., Parasitenkd., Infektionskr. Hyg., Abt. 1: Orig., Reihe A (1979), 244(2–3), 327–30; STN, File Chemical Abstracts, Abstract No. 9.

Rapid And Sensitive Detection of Point Mutations and DNA Polymorphisms Using the Polymerase Chain Reaction; Masato Orita, Youichi Suzuki, Takao Sekiya and Kenshi Hayashi, Genomics 5, pp. 874–879 (1989).

(List continued on next page.)

*Primary Examiner*—Kenneth R. Horlick
*Assistant Examiner*—Janell E. Taylor
*Attorney, Agent, or Firm*—Evenson, McKeown, Edwards & Lenahan, P.L.L.C.

[57] ABSTRACT

The object of the present invention is to provide a method capable of analyzing the presence or absence of a target DNA sequence, the level and sequence characteristics thereof at a high sensitivity, and a device therefor, wherein the overall process from pretreatment to the recovery of DNA information and the analysis thereof can be completed in a speedy fashion by the simple device structure and procedures.

Therefore, by preparing a single-stranded DNA fragment of a target DNA region, detecting the change in the absorbance of the single-stranded DNA sample while changing the denaturing condition of the conformation of the single-stranded DNA fragment by a denaturing condition regulatory means, and analyzing the curve of the change in the absorbance over the modification in the denaturing condition, the sequence information of the single-stranded DNA, namely the target DNA, can be generated in a rapid and simple manner.

15 Claims, 13 Drawing Sheets

OTHER PUBLICATIONS

Thermodynamics of RNA Folding in a Conserved Ribosomal RNA Domain, Lance G. Laing and David E. Draper, Academic Press Limited 1994, pp. 560–576.

Nomenclature For Factors of the HLA System, Immunogenetics, 1990, pp. 131–140.

The Effect of Nucleotide Substitution on DNA Denaturation Profiles, I.V. Razlutskii, L. S. Shlyakhtenko and Yu. L. L. Lyubchenko, Nucleic Acids Research, vol. 15, No. 16, 1987, pp. 6664–6677.

Generation of Single–Stranded DNA by the Polymerase Chain Reaction and its Application to Direct Sequencing of the HLA–DQA Locus, U. Gyllensten & H. Erlich, Pro. Natl. Acad. Sci. USA, vol. 85, pp. 7652–7656, Oct. 1988.

Comparative Studies on the Secondary Structure of Ovalbumin Messenger RNA and Its Complementary DNA Transcript; Nguyen T. Van et al.; Biochemistry, vol. 16, No. 18, 1977, pp. 4090–4100.

F–SSCP: Fluorescence–Based Polymerase Chain Reaction–Single–strand Conformation Polymorphism (PCR–SSCP) Analysis; Reiko Makino et al.; PCR Methods and Applications, Aug. 1992, vol. 2, No. 1, pp. 10–13.

Detecting Single–Base Mutations, Jane Prosser, Tibtech, Jun. 1993, vol. 11, pp. 238–246.

DNA ANALYZING METHOD AND DEVICE THEREFOR

BACKGROUND OF THE INVENTION

The present invention relates to a method for analyzing DNA information in the fields of clinical diagnosis and life science, and a device therefor.

In the rapidly progressing technology of DNA analysis, recently, significant attention has been focused on the analysis of information of DNA/RNA sequence in the fields of clinical diagnosis and life science. In the field of life science, for example, advances have been made for determining the entire nucleotide sequence of a variety of animal and plant DNAs, as illustrated by the Human Genome Project. Thus, the coding region of a novel protein and the regulatory site of the expression thereof have been analyzed gradually, involving also the elucidation of pathogenic genes such as oncogenes and the like.

In the field of clinical diagnosis, alternatively, the introduction of the technology of DNA analysis has been accelerated toward the identification of a variety of etiology and laboratory tests, on the basis of the fruitful results of these research works. The diagnosis of infectious diseases including viral hepatitis type C and AIDS (acquired immunodeficiency syndrome) due to HIV (human immunodeficiency virus) infection is one example of the fields for which the introduction of DNA diagnosis has been highly desired because of the high detection sensitivity required therefor and because of the relation between the infectious performance of these viruses (retroviruses) and the DNA/RNA polymorphism. For the laboratory tests of tumor cells, which are now dependent on empirical pathological diagnosis, and for the tests of the HLA (human leukocyte antigen) type with the sample number rapidly increasing from the demand of the registration at the myeloid bank, the introduction of the technology of DNA analysis has been desired to give accurate and precise information.

Great progress has been made recently in the DNA analysis technology desired in such fields, wherein a method for separating a slight difference in DNA sequence utilizing the difference in the conformation of a single-stranded DNA during electrophoresis has been developed, in addition to the conventional DNA sequencing and hybridization methods. As introduced in Genomics, Vol. 5, pp. 874–879, 1989, for example, the method designated as SSCP (Single Strand Conformation Polymorphisms) has been drawing attention as a technique for detecting even a single base substitution at a high sensitivity. The separating method detects the difference in sequence by detecting the difference in the conformation as the difference in the mobility on gel electrophoresis, with attention focused on the finding that leaving DNA, normally composed of a pair of complementary double strands, in a single strand state, typically, the single-stranded DNA autonomously associates by itself within the molecule under appropriate conditions (ion strength, temperature and the like) and forms a certain conformation specific to the sequence, which conformation varies depending on the sequence.

The method detects the difference in DNA at a high sensitivity, but because electrophoresis is employed in the process of separation, such a long period of time is required for the separation that a high throughput is realized only with much difficulty. The selection of the conditions for efficiently reflecting the difference in DNA sequence over the difference in the mobility on electrophoresis is difficult. Still furthermore, the method is hardly automated, and additionally, the method involves another drawback in requiring the separation in some case under a plurality of conditions so as to thoroughly separate the entire polymorphism.

A method called denaturant gradient gel electrophoresis for detecting a slight difference in DNA sequence has also been proposed, but because the method also employs electrophoresis, it has the same drawbacks as described above.

It has been known that the difference between the denaturing conditions of a double-stranded DNA with a completely complementary sequence and the conditions of a double-stranded DNA with an almost complementary but not completely complementary sequence can be detected as the difference in absorbance change when such double-stranded DNA is denatured into a single-stranded DNA (melting curve) (for example, see I. V. Razlutuskii, L. S. Shlyakhtenko and Yu. L. lyubchenko: Nucleic Acids Research, Vol. 15, No. 16, pp. 6665–6676 (1987)). Furthermore, it has been known that the type of a single-stranded RNA forming conformation (hair pin, stem, loop structure, etc.) can be detected and identified by the change in the absorbance when the base pairing of the single-stranded RNA is denatured (melting curve) (for example, see L. G. Laing and D. E. Draper: J. Mol. Biol. (1994) 237, 560–576).

According to these methods, an electrophoresis procedure is not required after a sample is collected, so that these methods are advantageous in that the procedures are simple and the measurements are easily carried out as an optical measurement, with higher reliability.

Additionally, a technique has been proposed, comprising optically measuring and detecting the phenomenon that when a double-stranded DNA having a completely complementary sequence and a double-stranded DNA having a nearly completely but not completely complementary sequence are denatured, the fluorescent energy transfer induced by two types of fluorophors individually labeling each of the complementary strands is eliminated, thereby detecting the difference in the sequences of the two types of DNAs which are not completely complementary (Japanese Patent Laid-open No. Hei 7-31500). Because no electrophoresis procedure is then required after a sample is collected, the same advantage is achieved as described in the aforementioned example.

However, it is only sequence compositions (GC contents, etc.) or deletion/insertion of bases that these methods can detect. The identification of detailed differences in sequence, particularly DNA polymorphism including single-base substitution, is substantially difficult by using these methods. These methods require the regulation of denaturing conditions to be carried out at such an extremely low rate that the methods have not been able to achieve the detection and determination at a high throughput.

Furthermore, no examination has been made about direct optical analysis of DNA polymorphism including single-base substitution in a single-stranded DNA.

SUMMARY OF THE INVENTION

In order to overcome the above-mentioned problems and disadvantages, in accordance with the present invention, the melting curve of the conformation of a single-stranded DNA is directly detected, whereby a more precise and practical method of signal processing is provided along with a device therefor with a simplified structure.

For separation and analysis of a single-stranded DNA of a target DNA region including a heterozygote type having more than two DNA types in one cell, the method of the present invention comprises memorizing the melting curves of all known types of polymorphism (template curves) comparing the signal curve of a sample with such single template curve or with all the curves prepared via linear binding of a plurality of the template curves in combination, and determining that the DNA type, namely the sequence characteristics of the measured single-stranded DNA fragment, is defined as a combination of the template curves, providing that the RMS between the signal curve and the combination is the smallest below a given value.

For the DNA analysis by PCR for clinical diagnosis, the sequence information of the target DNA fragment together with the amount of the PCR product, should be obtained. Therefore, the present invention is designed advantageously so as to bring about simultaneously all the information mentioned above via the quantitative measurement of the melting curve.

By providing a sample holding apparatus to hold the sample and regulate the sample temperature with a larger surface/volume ratio, the denaturing rate is increased for measurement. Consequently, it has been found that the melting curve of a single-stranded DNA during the temperature elevation for resolving the conformation draws a different curve from the melting curve during the temperature decrease for forming the conformation, which indicates the presence of hysteresis. By processing the data with a signal processor identical to what has been described above, DNA polymorphism with single-base substitution can be analyzed.

It has been found that, with the use of an intercalating agent, such as ethidium bromide which can shift the fluorescent wave length after intercalating to the DNA base pairing, the intensity of the fluorescence emitted from the interaction of the single-stranded DNA with the intercalating agent during the irradiation of the excitation beam changes corresponding to the denaturation of the single-stranded DNA. Therefore, by measuring the intensity and processing the data with a signal processor identical to what has been described above, the sequence information of the single-stranded DNA fragment can be yielded.

BRIEF DESCRIPTION OF THE DRAWINGS

FIG. 14(b) is a cross-sectional view along line XIV—XIV of FIG. 14(a);

DESCRIPTION OF THE PREFERRED EMBODIMENT

The present invention will now be illustrated hereinbelow in one example.

Figure 1:
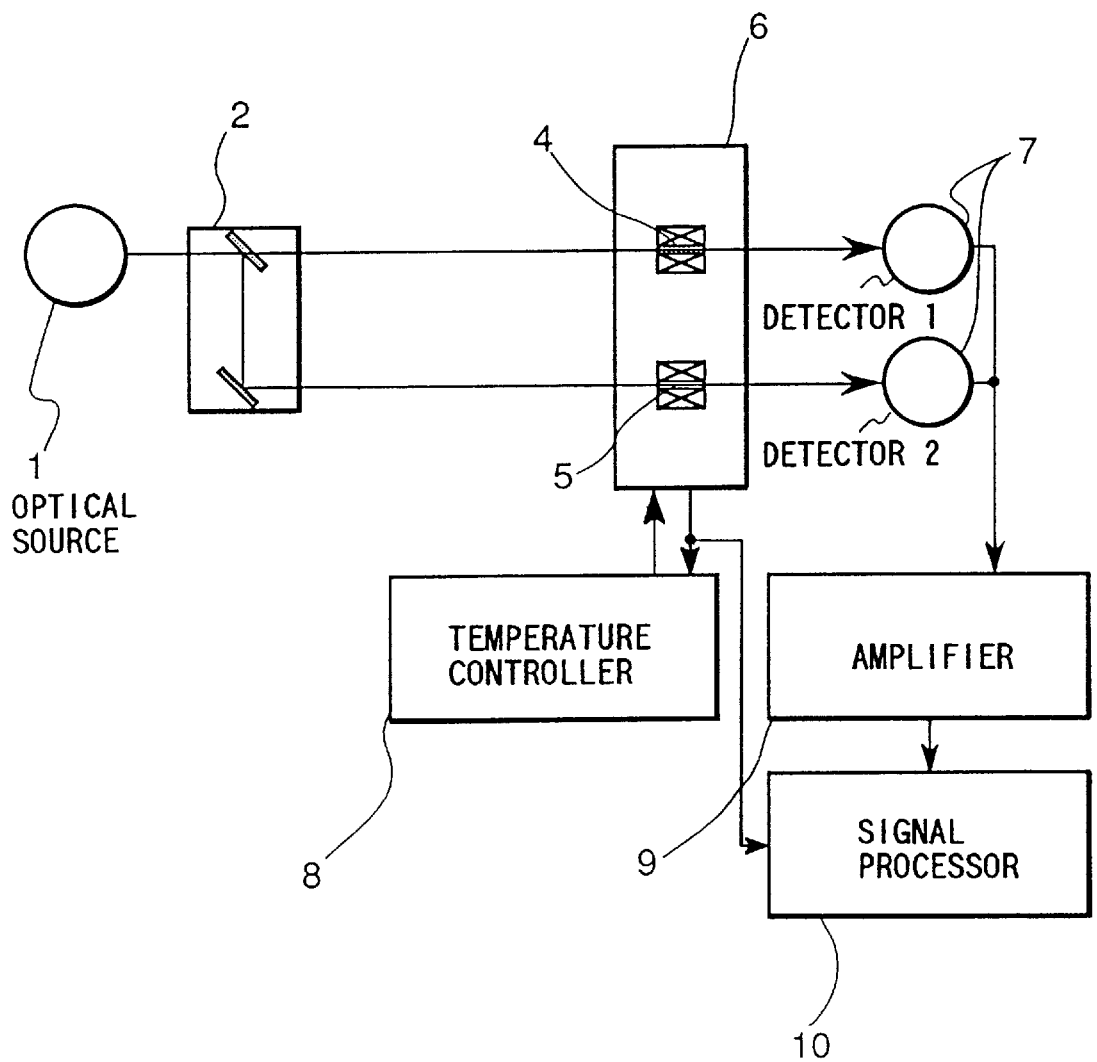
FIG. 1 is a block diagram of the structure of a detector of a first example in accordance with the present invention.
Figure 2A:
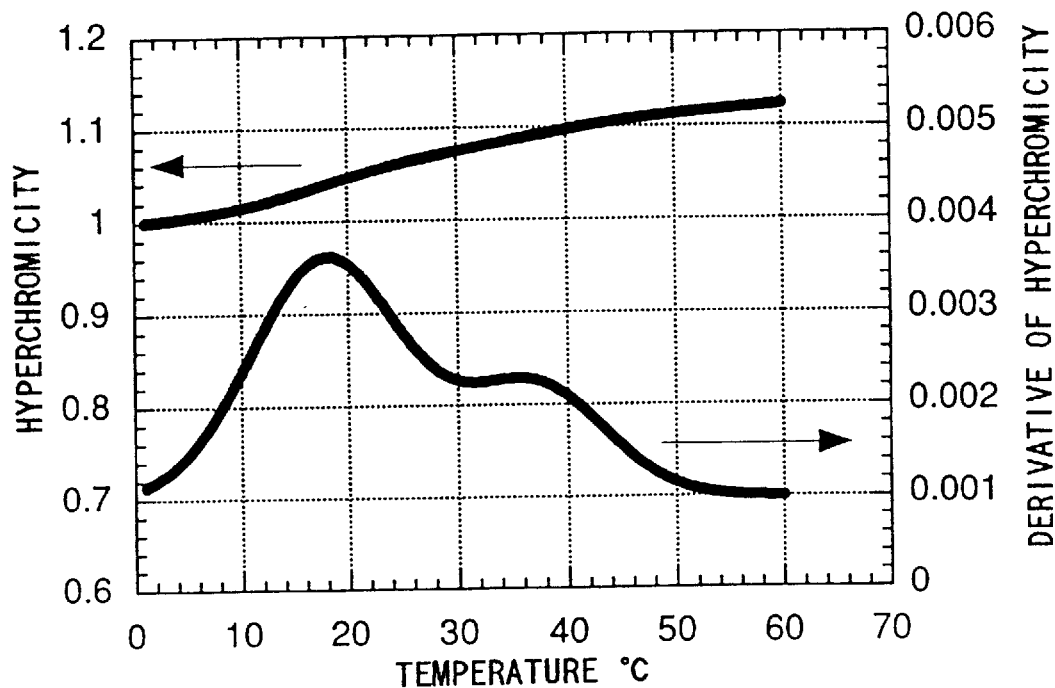
FIGS. 2(a) and (b) are graphs of the absorbance data and differential absorbance data obtained from the temperature differentiation of the absorbance data, representing the melting curve of a single-stranded DNA of the known type DQA1*0101 of DNA in the exon 2 of the HLA-DQA1 region.
Figure 2B:
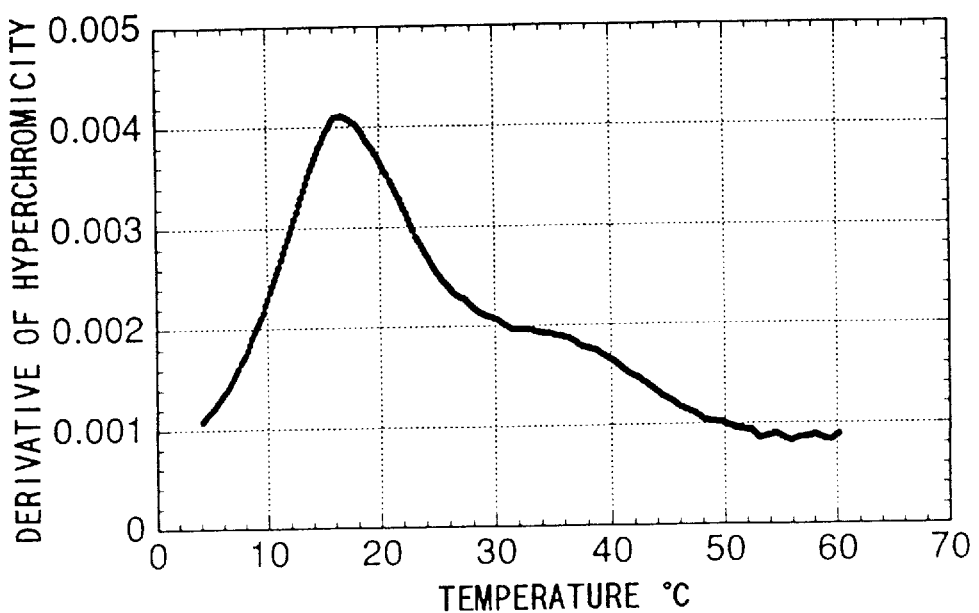
Figure 3A:
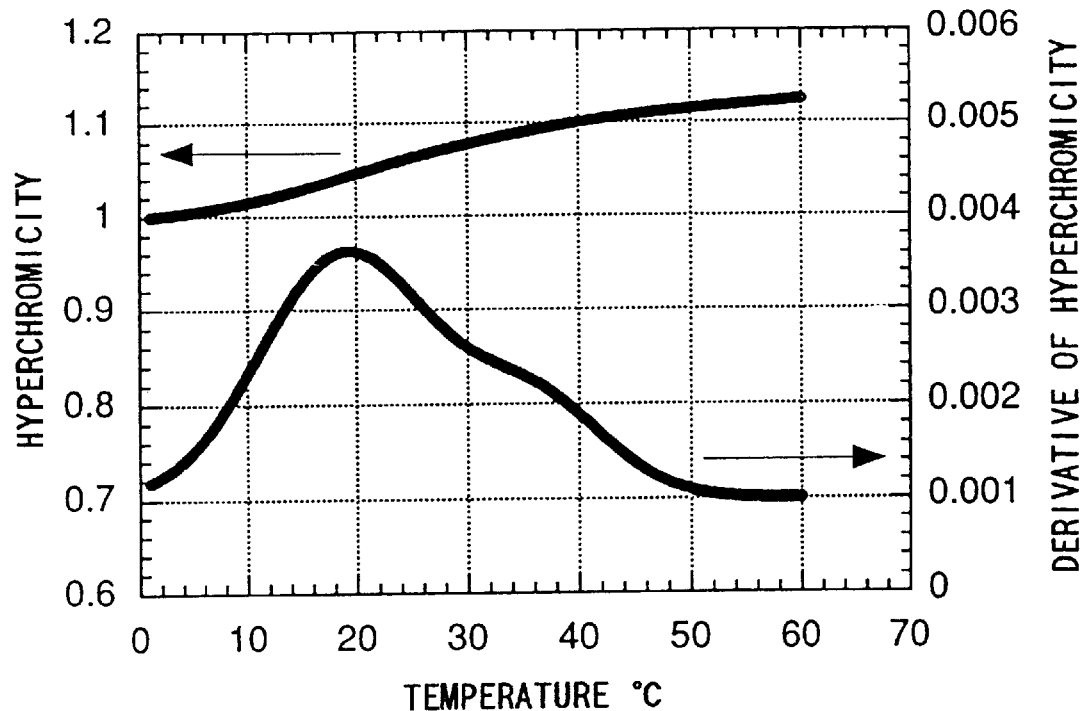
FIGS. 3(a) and (b) are graphs of the absorbance data and differential absorbance data obtained from the temperature differentiation of the absorbance data, representing the melting curve of a single-stranded DNA of the known type DQA1*0102 DNA in the exon 2 of the HLA-DQA1 region.
Figure 3B:
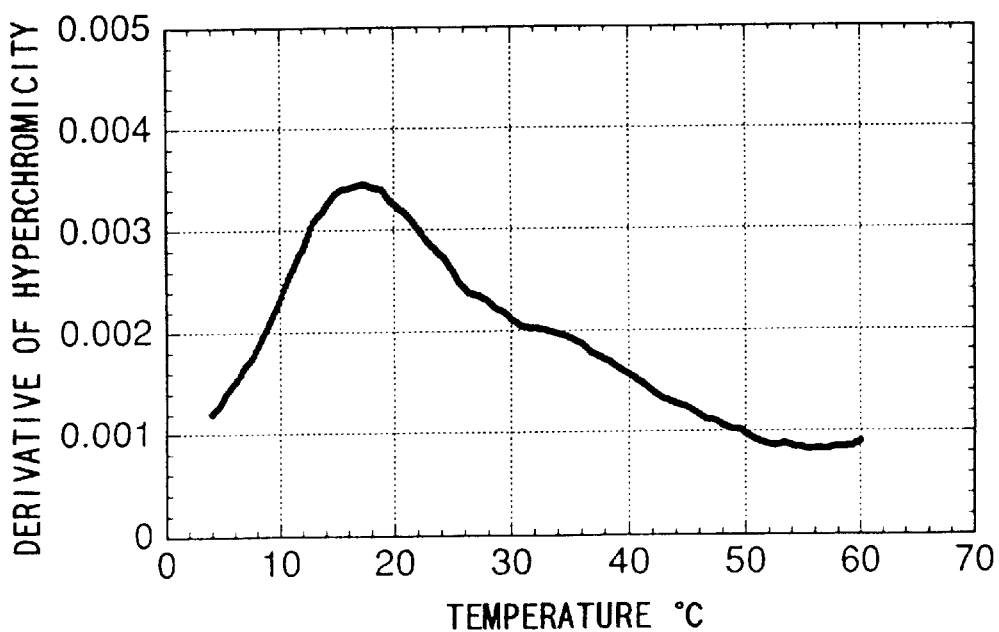
Figure 4A:
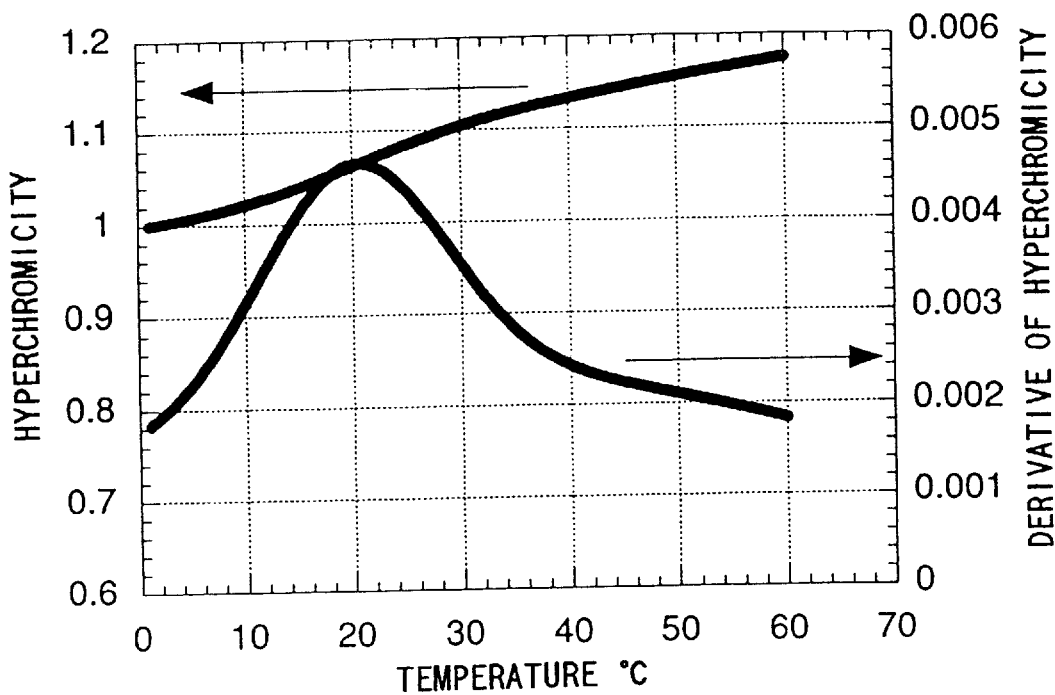
FIGS. 4(a) and (b) are graphs of the absorbance data and differential absorbance data obtained from the temperature differentiation of the absorbance data, representing the melting curve of a single-stranded DNA of the known type DQA1*0103 DNA in the exon 2 of the HLA-DQA1 region.
Figure 4B:
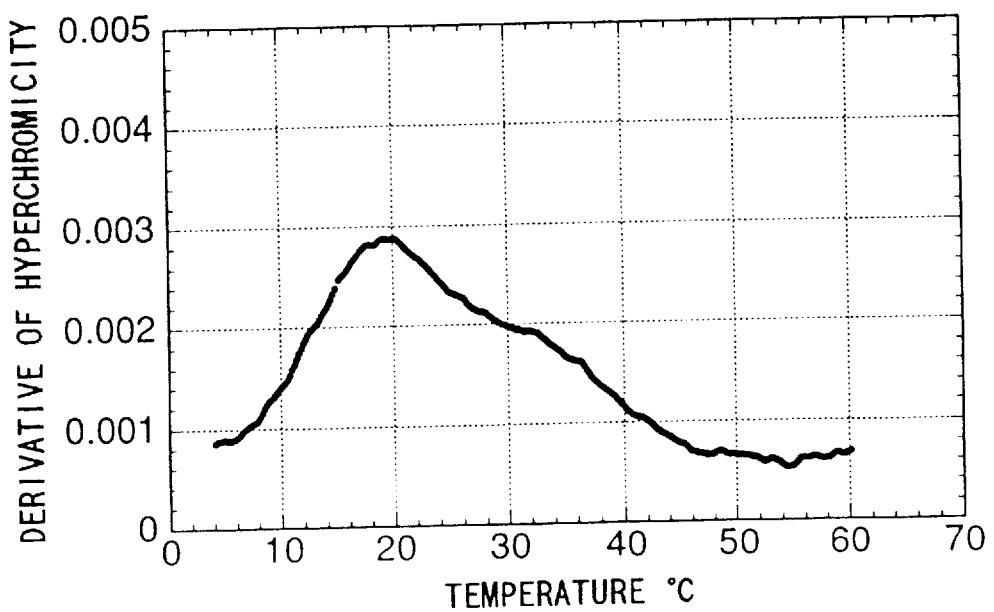
Figure 5A:
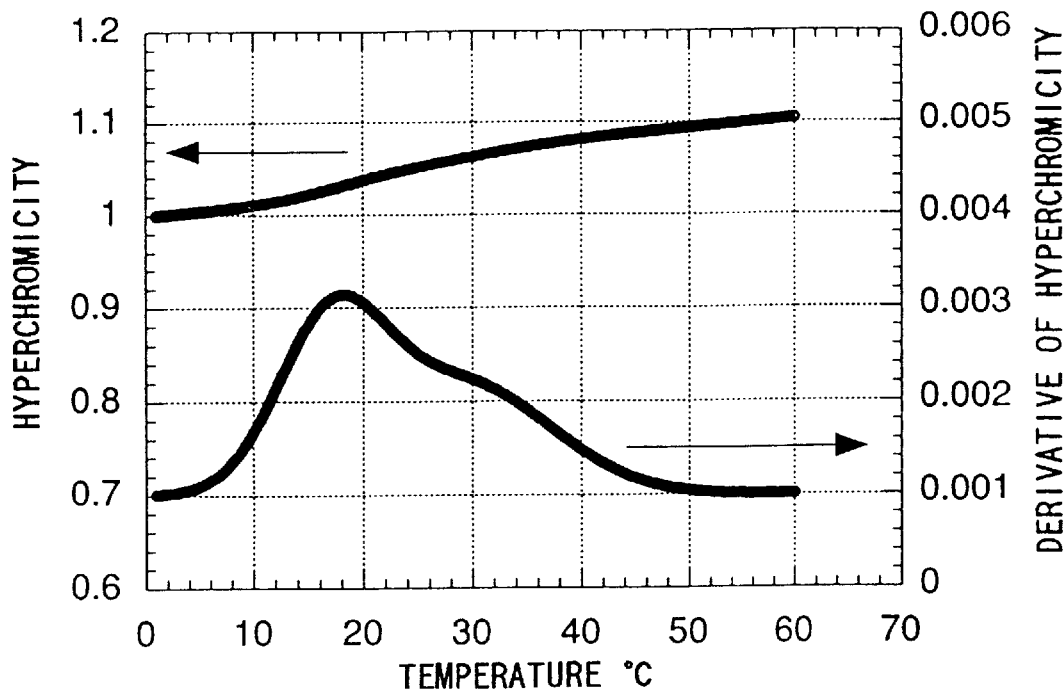
FIGS. 5(a) and (b) are graphs of the absorbance data and differential absorbance data obtained from the temperature differentiation of the absorbance data, representing the melting curve of a single-stranded DNA of the known type DQA1*0301 DNA in the exon 2 of the HLA-DQA1 region.
Figure 5B:
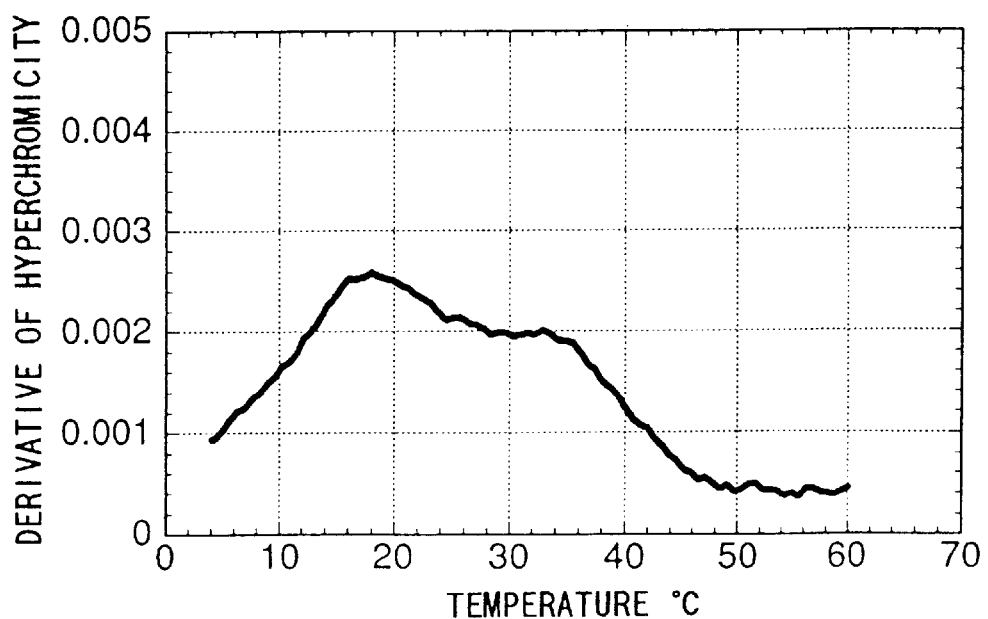
Figure 6A:
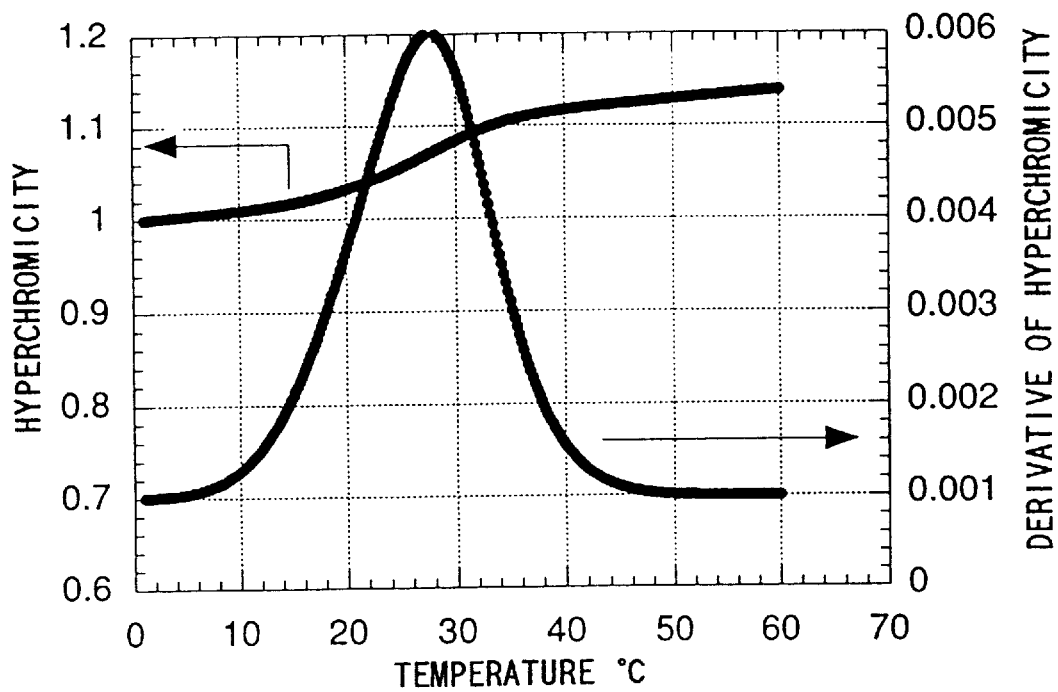
FIGS. 6(a) and (b) are graphs of the absorbance data and differential absorbance data obtained from the temperature differentiation of the absorbance data, representing the melting curve of a single-stranded DNA of the known type DQA1*0401 DNA in the exon 2 of HLA-DQA1 region.
Figure 6B:
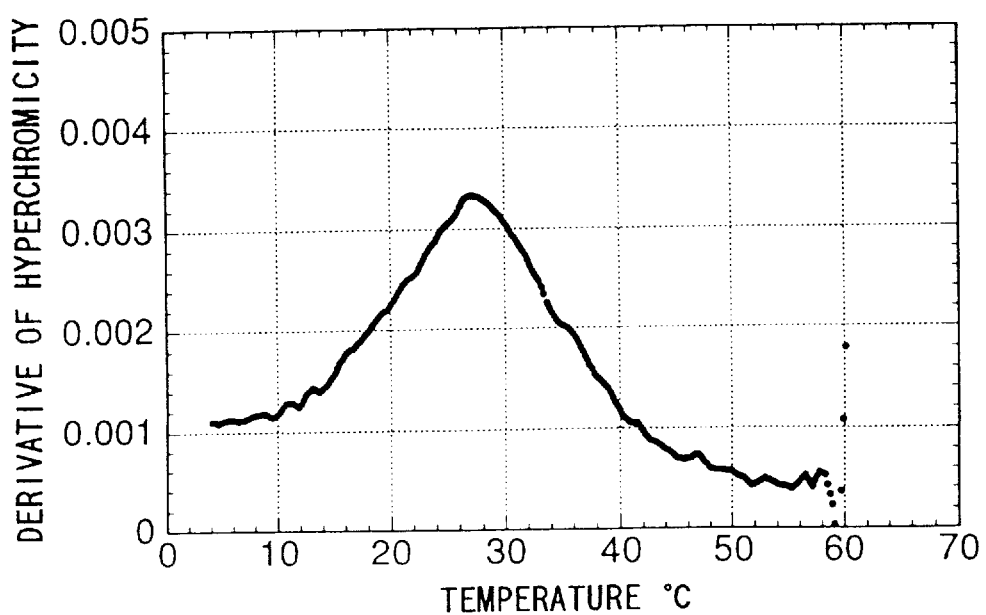
Figure 7A:
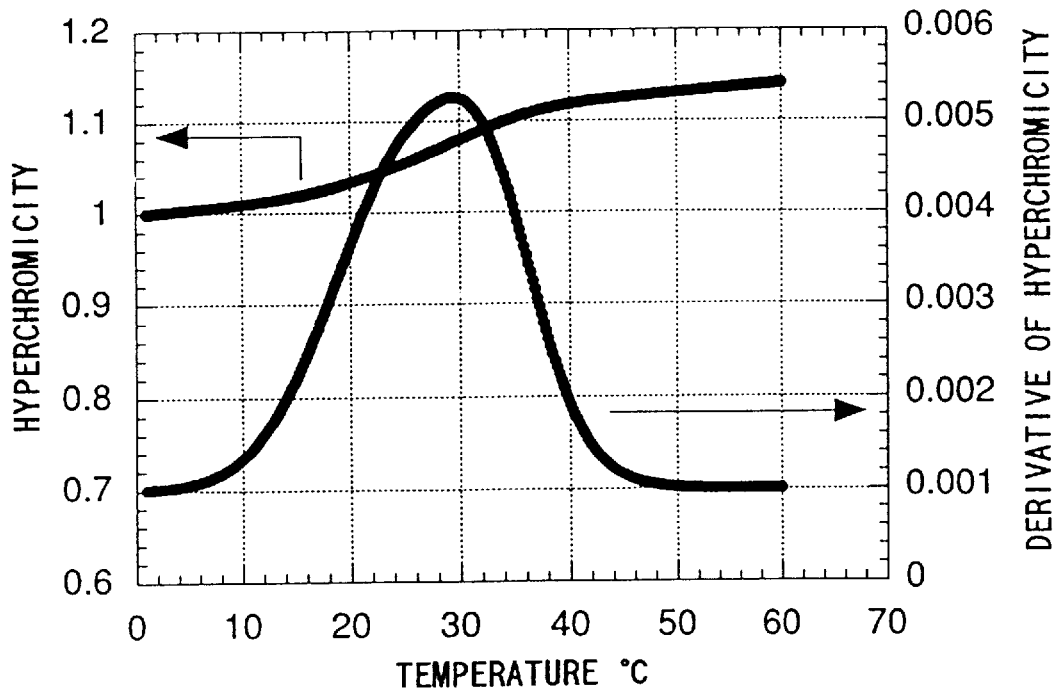
FIGS. 7(a) and (b) are graphs of the absorbance data and differential absorbance data obtained from the temperature differentiation of the absorbance data, representing the melting curve of a single-stranded DNA of the known type DQA1*0601 DNA in the exon 2 of HLA-DQA1 region.
Figure 7B:
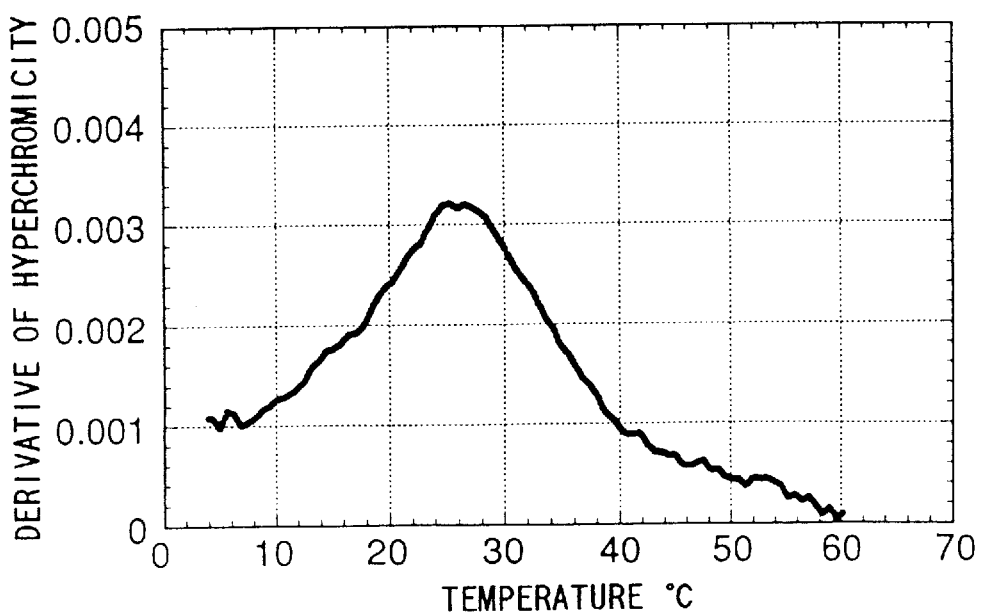

FIG. 1 is a block diagram of the fundamental structure of the DNA analyzer in accordance with the present invention. An ultraviolet ray (of a wave length of 260 nm) from light source 1 is divided into two beams at an optical system 2, which beams are then individually incident into sample part 4 and control part 5, both being placed in cell holder 6. Thereafter, the individual beams collimated with optical systems (not shown) are detected with photomultiplier 7, and are then passed through amplifier 9 and processed with analytical signal processing device 10. The cell holder 6 can control the temperatures of the sample part 4 and the control part 5, following the temperature profiles programmed optionally with temperature controller 8. Temperature control can be done at an optional rate of temperature increase or decrease. The temperature in the cell holder 6 is measured with a temperature sensor (not shown), and input to the feedback temperature controller 8 and the signal processing device 10 simultaneously. Because it is required that the temperature of some sample should be controlled within the range from −20° C. to 100° C., the cell holder 6 has such a structure in which dry air flows from the bottom of each sample holding cell 4 and 5 to the top thereof so as to prevent the occurrence of bedewing on the surface of the both cells.

The control part 5 is arranged to correct the absorption of a buffer solution dissolving a sample at the sample part 4 and the absorption of the sample cell to determine the net DNA absorption. This is a routine technique in spectrometry, and the data in examples described below all use the correction.

Using the device described above, DNA polymorphism analysis will be illustratively described hereinbelow.

In the present Example, single-stranded DNA of HLA (human leukocyte antigen) class II is studied: DQA1 region was amplified using asymmetric-PCR method from genomic DNA extracted from human blood cells. Then, the DNA polymorphism analysis (DNA typing) of the region was carried out.

By the standard procedure, a DNA sample solution with the extracted genomic DNA, a PCR buffer solution containing a final 10 mM concentration of Tris-HCl (pH 8.3), 50 mM KCl, 1.5 mM $MgCl_2$, 0.02% gelatin, and 200 $\mu$M of each of deoxyribonucleotide triphosphates (dATP, dCTP, dGTP, and dTTP), 2.5 U Taq polymerase, 20 pmol of each of the two types of primers GH 26 and GH 27 corresponding to the HLA-DQA1 region to be analyzed (Ulf B. Gyllensten and Henry A. Erlich; Proceedings of the National Academy of Sciences of USA, Vol. 85, pp. 7652–7656, October 1988) were mixed together in a test tube, followed by overlaying mineral oil on the mixture. The PCR cycling condition was 27 cycles of 94° C. (1 minute), 57° C. (1.2 minute) and 72° C. (1 minute) in this order.

Using 1/100 of the reaction product, asymmetric PCR was done. The asymmetric PCR solution was almost the same as described for PCR, except that the amounts of the primers were modified such that GH 26 was 10 pmol and GH 27 was 1 pmol. The PCR cycling condition was 15 cycles of 94° C. (1 minute), 57° C. (1.2 minute) and 72° C. (1 minute) in this order.

The reaction product was desalted and concentrated with a microfilter (Microcon™ 30, manufactured by Grace Japan), which was then dissolved in the TNE buffer (10 mM Tris-HCl, 1 mM EDTA (pH 8.3), 30 mM NaCl). The resulting product was defined as a sample solution.

In the present Example, asymmetric PCR was used for preparing a single-stranded DNA, but other methods may be used as well, including a method comprising PCR amplifying a double-stranded DNA and thereafter digesting one single-stranded DNA with $\lambda$ exonuclease ($\lambda$ exonuclease method) and a method comprising PCR amplification in the state where either one of the PCR primers is immobilized on membrane and thereafter washing off the single-stranded DNA not immobilized on the membrane while elevating the temperature to the melting temperature (membrane method). Although the membrane method requires immobilizing a predetermined primer on membrane, the method can prepare a single-stranded DNA at a high purity in a simple manner. Additionally, the method is suitable for automation.

Placing the sample solution at the sample part 4 while placing the TNE buffer as the control solution at the control part 5, the sample temperature was once decreased to 0° C. Subsequently, the temperature was elevated to 60° C. at an elevation rate of 1° C./min.

FIGS. 2 to 7(a) and (b) depict the melting curves of the single-stranded DNAs of the known six types (DQA1*0101, DQA1*0102, DQA1*0103, DQA1*0301, DQA1*0401, DQA1*0601; The WHO Nomenclature Committee for Factors of the HLA System, 1989, Immunogenetics, 31: 131–140, 1990) of the HLA-DQA1 region DNA (242 bp or 239 bp), as absorbance data and differential absorbance data by temperature (the data of the other two types, i.e. DQA1*0201 and DQA1*0501, were not shown herein because the inventors could not obtain their homozygote samples). In each of the figures (b), only differential absorbance data are shown. One base is different between the types DQA1*0101 and DQA1*0102; three bases are different between the types DQA1*0101 and DQA1*0103; and two bases are different between the types DQA1*0102 and DQA1*0103. Twenty-seven bases are different between the types DQA1*0101 and DQA1*0301. The types DQA1*0401 and DQA1*0601, by three bases shorter than the other types, have the sequences difference in twenty bases or more from the sequence of DQA1*0101, but only one base is different between these types DQA1*0401 and DQA1*0601.

Still further, the individual figures (a) and (b) depict the results of the analysis of the same samples, but the figure (a) depicts the results of the analysis obtained until the application of the priority of the present invention, while the figure (b) depicts the results of the analysis relatively recently obtained. The reason that the two figures do not completely agree with each other although the figures depict the analysis results of the same samples resides in the difference in the skill of analytical procedures and the data correction adopted for making up for the unskilled analytical procedures. The fact does not mean that the analysis has no reproducibility.

The figures show that groups with very different sequences, for example, a group of DQA1*0101–DQA1*0103 (type 1), a group DQA1*0301 (type 3) and a group of DQA1*0401 and DQA1*0601 (short type), have distinctively different characteristics in their melting curves. It is also shown that the type difference such as the difference in one base or two bases (for example, DQA1*0101–DQA1*0103, DQA1*0401, DQA1*0601), can be detected as a marked difference.

Figure 8:
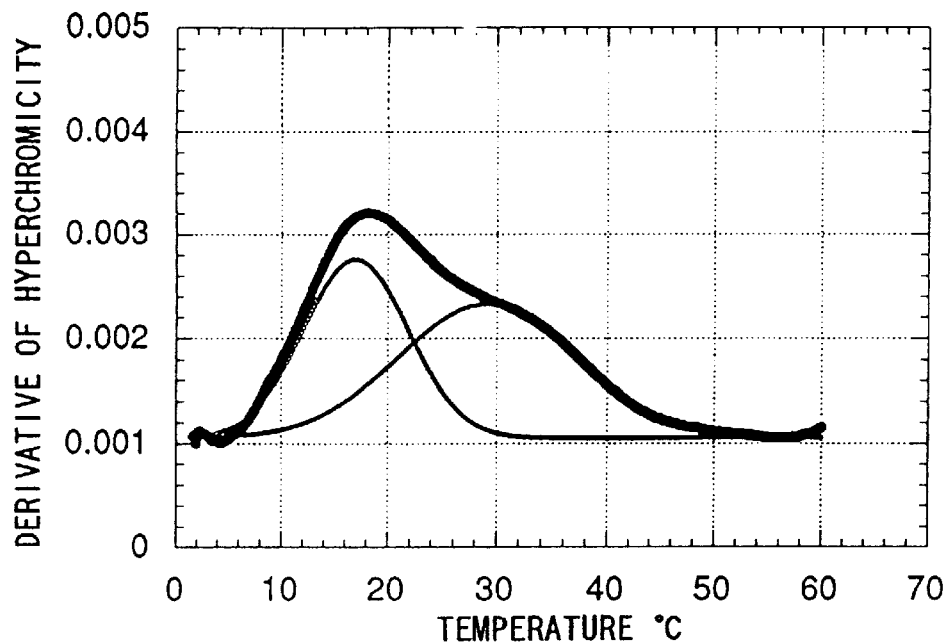
FIG. 8 is a graph of the derivative of the melting curve of the type DQA1*0301, after fitting with the Gaussian distribution curves.

FIG. 8 depicts the derivative of the melting curve of the type DQA1*0301, fitting with the Gaussian distribution functions. As is readily apparent in FIG. 8, the melting curve of the type DQA1*0301 can be satisfactorily fitted with the superposition of two types of Gaussian curves.

In other words, this indicates that by preparing the melting curves of the known DNA type and comparing the melting curve of a sample DNA with the melting curves of these known DNA type as the templates, the type of sample DNA can be identified. Furthermore, by fitting the Gaussian curve to the melting curve, this identification can be carried out numerically and more efficiently.

Table 1 collectively shows the amplitude (a), peak location (mean; $\mu$) and range (standard deviation; $\sigma$) of a plurality of the Gaussian curves fitted to the derivatives of the melting curves of the known six types depicted in FIGS. 2 to 7.

TABLE 1

| DNA Type | Number of Terms | a | $\mu$ | $\sigma$ |
|---|---|---|---|---|
| DQA1*0101 | 1 | 0.0026 | 18 | 10 |
|  | 2 | 0.0012 | 37 | 9 |
| DQA1*0102 | 1 | 0.0026 | 19.0 | 11 |
|  | 2 | 0.001 | 36.0 | 9 |
| DQA1*0103 | 1 | 0.0025 | 20 | 12 |
|  | 2 | 0.0013 | 34 | 39 |
| DQA1*0301 | 1 | 0.0017 | 17 | 7 |
|  | 2 | 0.0012 | 29 | 11.5 |
| DQA1*0401 | 1 | 0.0037 | 26 | 10 |
|  | 2 | 0.0015 | 29 | 5.5 |
| DQA1*0601 | 1 | 0.0037 | 26 | 10 |
|  | 2 | 0.0014 | 33 | 5.5 |

The number of terms in the Gaussian functions used for fitting is defined as a number where fitting error is saturated at minimum. As shown in the Table, the derivative of a melting curve corresponding to one of the types can be represented by its characteristic parameters (a, $\mu$, $\sigma$). Comparing the melting curve of an unknown DNA (type) with the melting curves of these known types of DNA poloymorphism as the templates via the comparison with the parameters shown in Table 1, permits the procedure to be done through automatic computer processing and also realizes a strict comparison through the mathematical process.

For the mathematical process, comparing a freshly measured input signal curve with one of the known melting curves preliminarily prepared or with all the curves preliminarily prepared by linearly binding a plurality of the template curves in combination, a template curve with the least statistical error or a combination of the template curves that give the linearly bound curve with the least statistical error should be defined as the sequence characteristics of a single-stranded DNA fragment prepared from the sample double-stranded DNA fragment.

Figure 9:
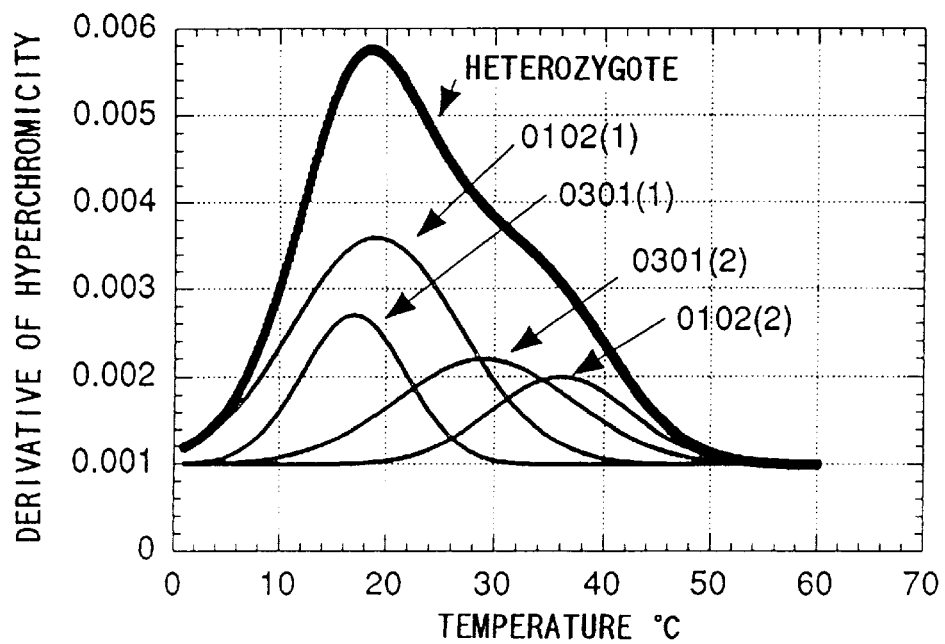
FIG. 9 is a graph of the derivative of the melting curve of a heterozygote sample of the types DQA1*0102 and DQA1*0301, representing the characteristic parameters of the curve.

FIG. 9 depicts the derivative of the melting curve of a heterozygote sample of 0102 and 0301(representing DQA1*0102 and DQA1*0301), together with the characteristic parameters of the curve. In such heterozygote sample, the derivative is represented as the superposition of template curves of the individual DNA type, which indicates that typing can be carried out on the principle of spectral analysis.

On the basis of the results of FIG. 9, Table 2 summarizes the parameters of the individual DNA types. More specifically, if a heterozygote DNA has the parameter values of $\mu$ (peak location) and $\sigma$ (standard deviation), being almost the same as those represented as the regression values shown in Table 2, the heterozygote DNA is of a heterozygote of two DNA types deduced from the values.

TABLE 2

| $\mu$ | Regression values | $\sigma$ | Regression values | DNA Types |
|---|---|---|---|---|
| $\mu 1$ | 16.9 | $\sigma 1$ | 6.89 | 0301 |
| $\mu 2$ | 19.0 | $\sigma 2$ | 11.0 | 0102 |
| $\mu 3$ | 28.9 | $\sigma 3$ | 11.5 | 0301 |
| $\mu 4$ | 35.9 | $\sigma 4$ | 9.0 | 0102 |

In the present Example, a satisfactorily accurate melting curve can be generated in a practical sense, at a temperature elevation rate of 5° C./min at maximum. In this case, the analysis time is about 10 minutes per sample, achieving speeding up by 20 fold or more compared with the conventional DNA sequencing and SSCP method (4 hours or more).

Figure 10:
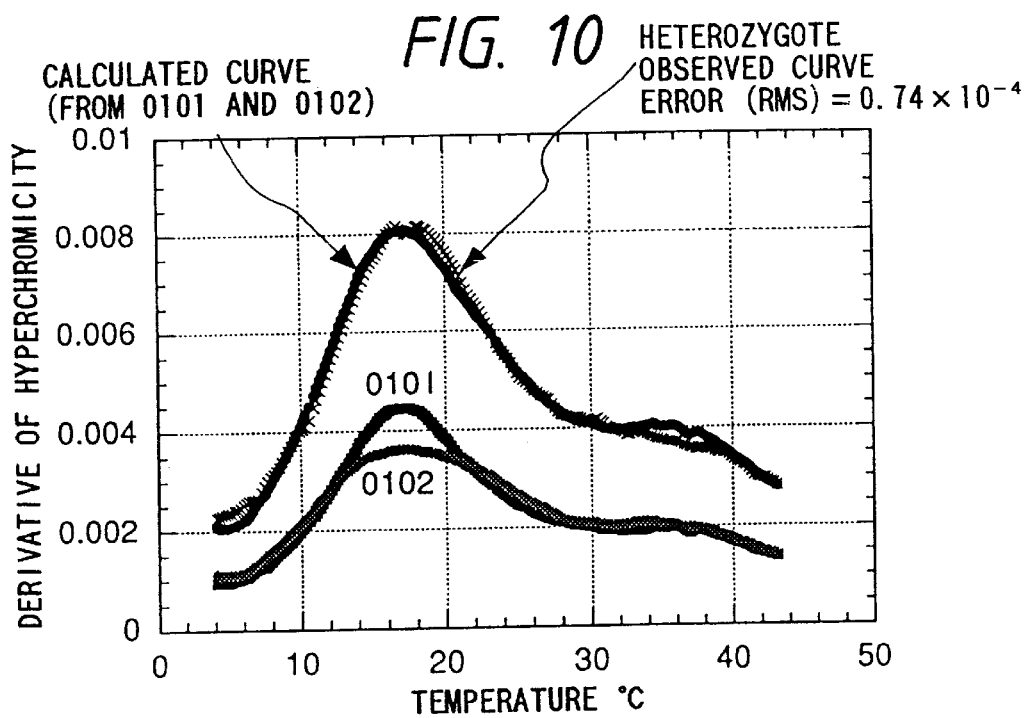
FIG. 10 are graphs of another analysis example of a heterozygote DNA.

FIG. 10 depicts another analysis example of a heterozygote DNA based on FIGS. 2(a) to 7(b). In the present Example, the melting curves of the eight types of DNA type in the HLA-DQA1 exon 2 region (242 p or 239 bp (3-bp depletion)) as the templates for individual sense strands should be measured preliminarily. The measured heterozygote curve from a sample agrees well with the synthetic curve of the template 0101 represented to the DQA1*0101 and the template 0102 represented to the DQA1*0102 (RMS=0.00008). Consequently, it is indicated that the sample can be identified as the heterozygote DNA of the two.

For the polymorphism analysis, it is necessary to determine to which type the DNA type of an analytical sample belongs and/or whether the DNA type is novel or not. Also, essentially, a heterozygote sample having a plurality of DNA types should be isolated and analyzed. In the present Example, however, accurate identification of a DNA type can be carried out in a smooth manner using a signal processor which memorizes the melting curves corresponding to all known types of polymorphism (template curves), compares a freshly measured input signal curve with one of a plurality of the template curves or with all the curves preliminarily prepared by linearly binding a plurality of the template curves in combination, and determines that a combination of the template curves that give the least RMS below a given value is the DNA type (namely, sequence characteristics) of the measured single-stranded DNA fragment. Furthermore, combinations with larger probabilities can be output in the order of smaller RMS.

As to the results shown in FIG. 10, the merit of this procedure is demonstrated in Table 3.

The combination with the least final error represents an accurate heterozygote combination, and the value of the error is almost the same as (rather smaller than) the reproducibility error in the measurement of the melting curve 5 times. Table 3 shows the reproducibility error and RMS of an accurate combination (the combination marked with double circles in the Table), along with the RMSs of some of the combinations with less error among the remaining combinations. For a heterozygote combination of sequences different by one base from each other, the DNA type with the highest probability of erroneous judgment is a homozygote type of each of the individual DNA types originally constituting the heterozygote type. As apparently shown in Table 3, it is indicated that significant difference is present between accurate and inaccurate judgments.

TABLE 3

| c.f. Hetero (DQA1*0101/0102) | |
|---|---|
| DNA types | Error (RMS) = $10^{-4}$ |
| ⊚0101/0102 hetero | 0.74 |
| 0101 homo | 1.28 |
| 0102 homo | 1.55 |
| 0101/0103 hetero | 2.56 |
| 0101/0201 hetero | 4.5 |
| Reproducibility error | 0.8 |

Figure 11:
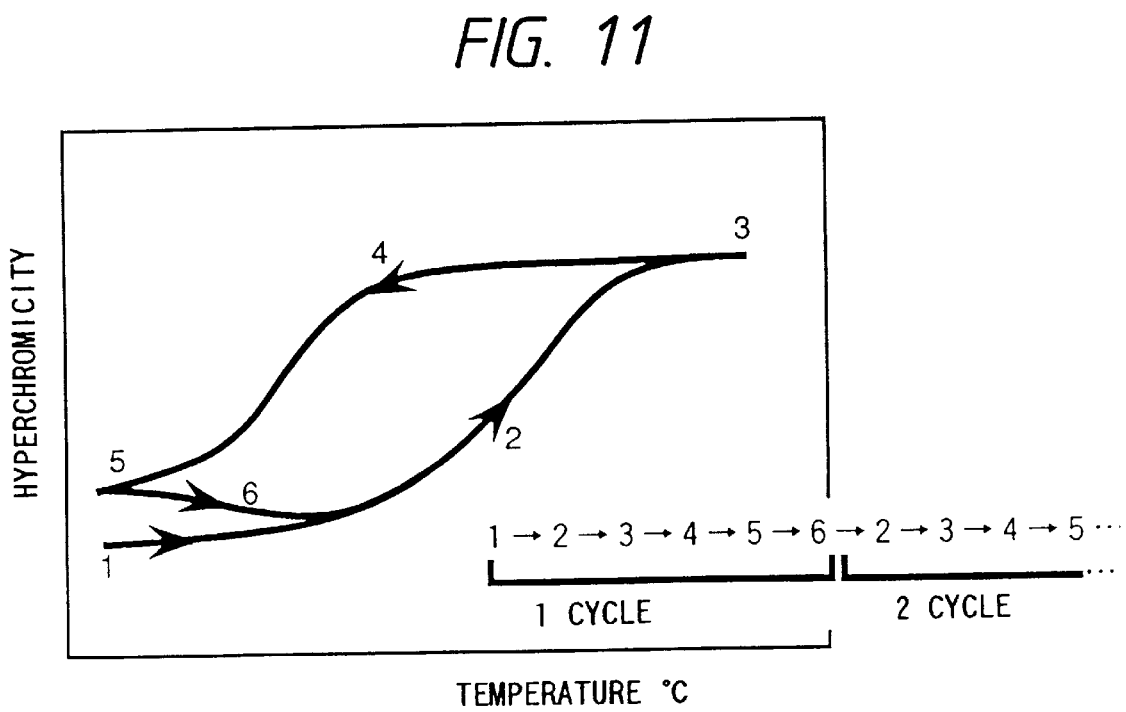
FIG. 11 depicts a measurement example of the hysteresis curve of a melting curve.

By substantially uniformly regulating the temperature of samples at a high speed, the dynamic response of the conformation of a single-stranded DNA fragment of some sample to the temperature change was identified in a range above 10° C./min of temperature elevation or decrease. More specifically, it was identified that during the denaturing and forming of the conformation (during temperature elevation and decrease, respectively), the melting curve drew a hysteresis curve (1→2→3→4→5→6→2→3→4→5→ . . . ) as shown in FIG. 11. Specific to the difference in sequence such as the substitution, depletion or insertion of bases, the hysteresis curve varies depending on the sample. This indicates that the method is not only applicable to the change in the absorbance but also to the hysteresis curve of the absorbance, wherein more accurate determination of such type at a higher speed can be done by comparing a measured hysteresis curve with the template hysteresis curves in the same manner as in the case of the signal processing method.

In such manner, the measurement of a sample was completed within one minute (for 50 seconds) at maximum speed, to generate a hysteresis curve at two cycles of temperature elevation and decrease. The hysteresis curve varies depending on the rate of temperature elevation. Therefore, if the rate of temperature elevation is set at an appropriate level depending on the type, an effective hysteresis curve corresponding to the DNA type can be produced. Thus, the DNA analysis can be effected on the basis of the dependency of the hysteresis curve on the rate of temperature elevation.

Figure 12:
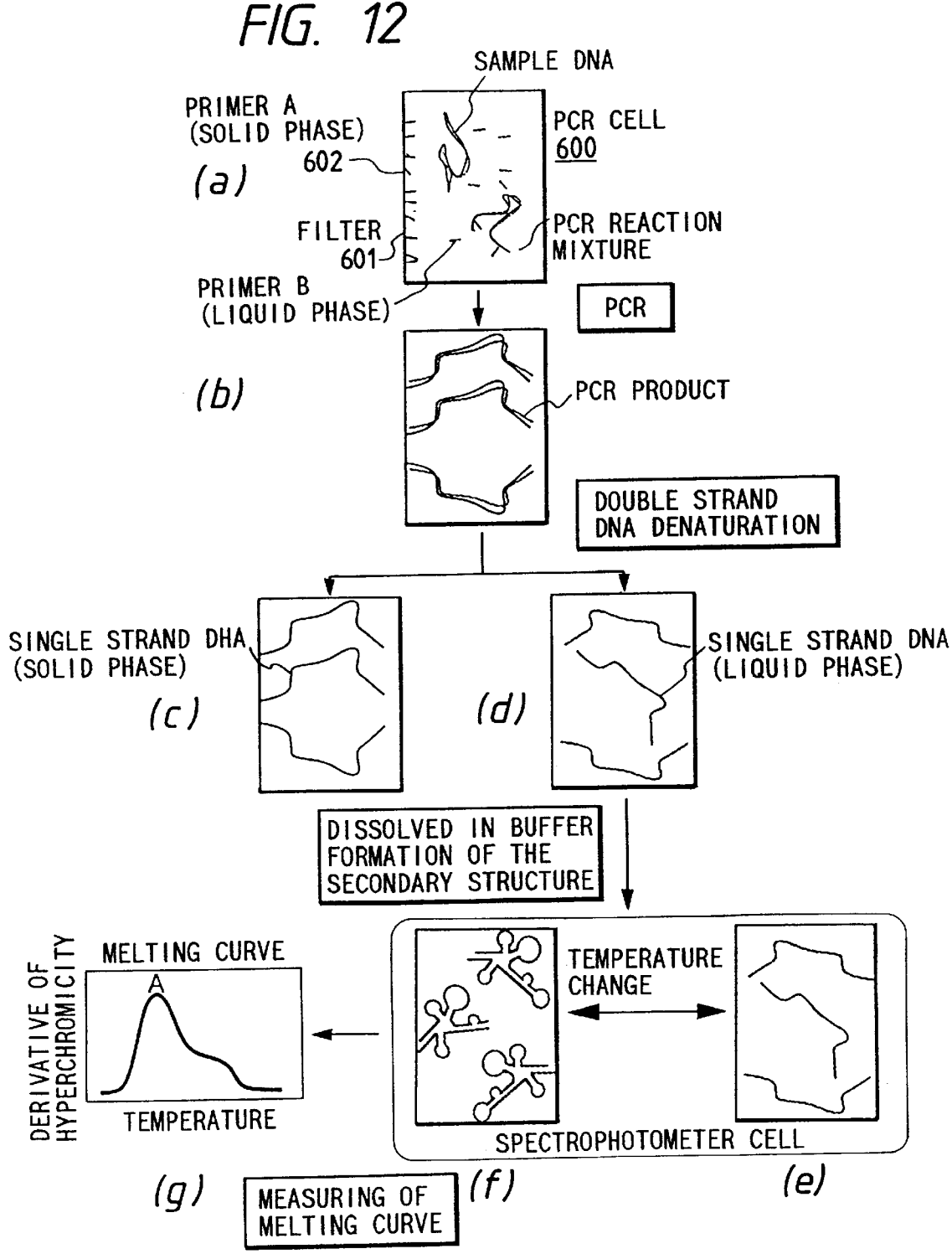
FIG. 12 is a schematic chart of the process flow of an example in accordance with the present invention.
Figure 13:
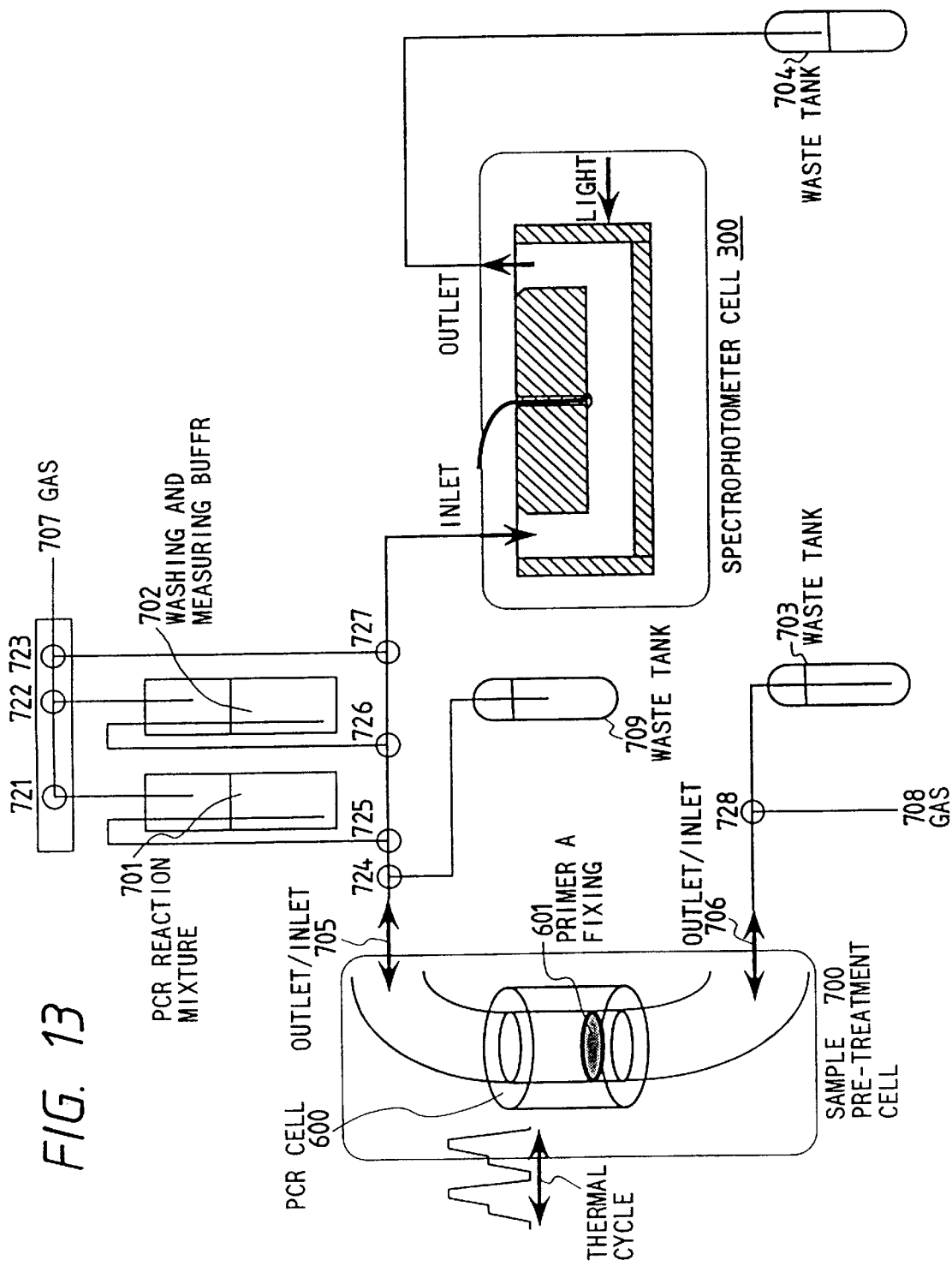
FIG. 13 is a schematic view of the structure of the detector of the first example in accordance with the present invention.

Then, examples of a device for DNA analysis are shown in FIGS. 12 and 13, for continuously carrying out a flow system from PCR as a preliminary treatment to the melting curve measurement.

Figure 14:
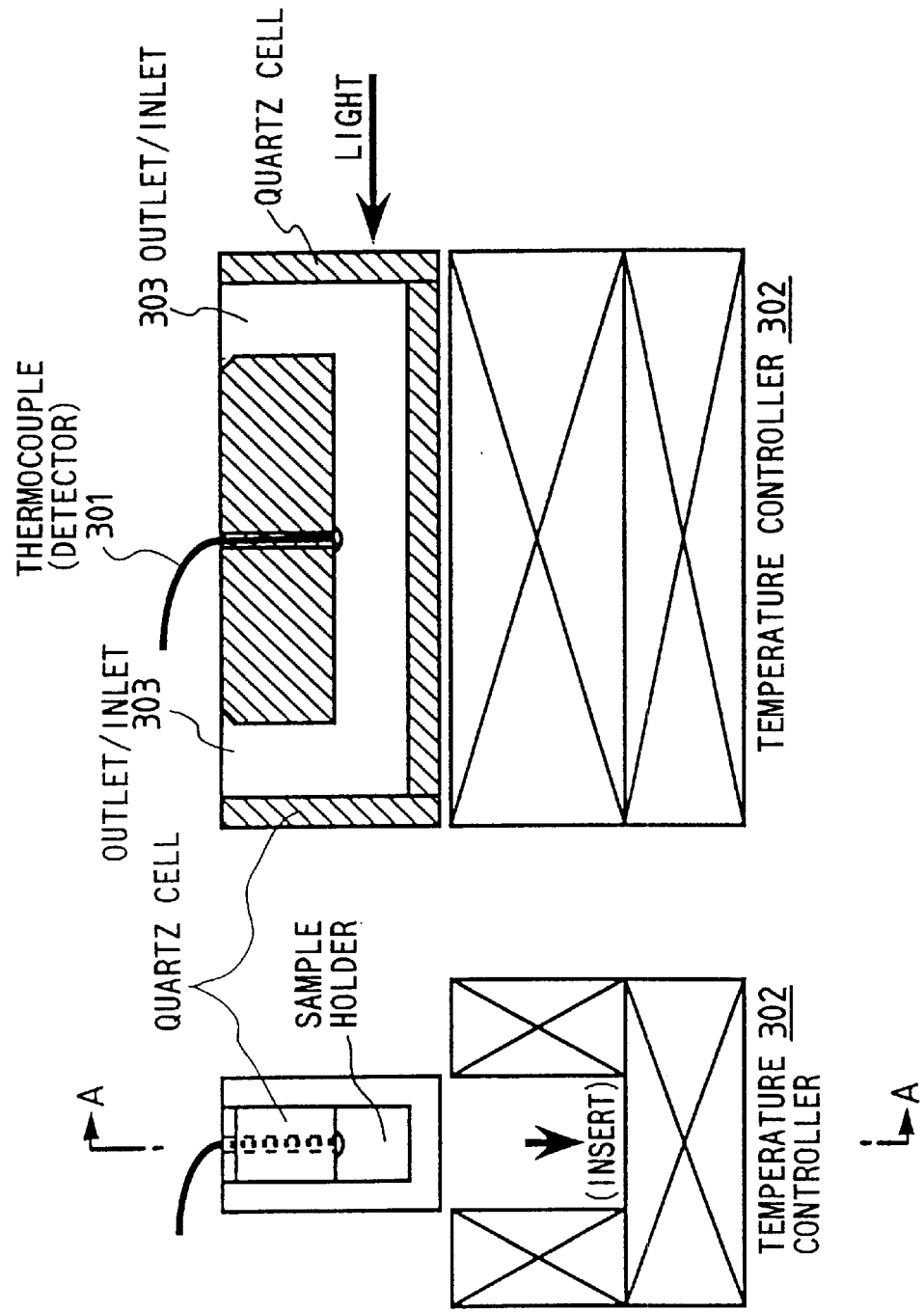
FIG. 14 (a) shows the structure of the spectroscopic cell of an example in accordance with the present invention.

FIG. 12 depicts the schematic chart of the process flow; FIG. 13 depicts the schematic view of the device structure; and FIG. 14(a) depicts the detailed structural view of the spectroscopic cell.

The reaction process progresses through the processes (a) to (g) shown in FIG. 12. As shown in step (a), PCR is carried out in PCR cell 600 immobilizing oligonucleotide A 602 as a PCR primer on porous filter membrane 601 on the bottom of the PCR cell. In the PCR cell 600, extracted and purified genomic DNA is placed as a sample, which is then mounted in the device of FIG. 13. As shown in (b) as the PCR progresses, a double-stranded DNA (PCR product) corresponding to the sample DNA is generated in the manner such that the single strand on the solid phase is fixed at one end on the filter membrane 601. The denaturing of the double-stranded DNA separates a free single-stranded DNA in the liquid phase as shown in (d) from the single-stranded DNA fixed at one end on the filter membrane (solid phase) as shown in (c). Dissolving the single-stranded DNA of the liquid phase in a buffer solution for measurement, and transferring the DNA solution into a spectroscopic cell, the temperature of the spectroscopic cell is controlled to regulate the state of a single-stranded DNA in the liquid phase (in the denatured state) as shown in (e) and the formation of the conformation as shown in (f). As shown in (g), the absorbance is measured through the spectroscopic cell, to prepare a melting curve.

FIG. 13 depicts the schematic view of the detector structure. As described below, after transferring a PCR solution, a washing buffer and a spectroscopic buffer through gates 705, 706 of sample pretreatment cell 700 into PCR cell 600, the PCR cell 600 is regulated at a given heat cycle. Porous filter 601 immobilizing primer A is placed in the PCR cell 600. In the sample pretreatment cell 700, the treatments (a) to (d) described in FIG. 12 are carried out.

On the porous filter 601 inside the PCR cell 600 is immobilized oligonucleotide A (10 pmol) as a PCR primer, and then, the extracted and purified genomic DNA (100 ng) is placed as a sample in PCR solution tank 701. Gas is transferred through gas source 707 and valves 723, 722, 721 into the PCR solution tank 701, while the PCR solution (50μ 1) is transferred through valves 725, 724 into the PCR cell 600. In this case, the PCR solution was made of a mixture solution of primer (oligonucleotide ) B (10 pmol), 10 nmol each of deoxyribonucleotide triphosphates (dNTP: dATP, dCTP, dGTP, dTTP) and a heat-resistant DNA polymerase (Taq polymerase) (1 unit) in a buffer solution containing 50 mM KCl, 10 mM Tris-HCl (pH 8.3), 1.5 mM $MgCl_2$, gelatin of 0.001% (as a final concentration).

In this state, PCR is performed while regulating the temperature of the PCR cell 600 in hot air or cold air. The PCR cycling condition is 25 cycles of 94° C. for 30 minutes, 55° C. for 1 minute 72° C. for 30 seconds and in this order. The total reaction time was 50 minutes. The time period required for the PCR is possibly shortened as short as about 20 minutes, by making the cell shape into a thinner form and enlarging the surface/volume ratio. By closing the valves 724, 728, the vaporization of the reaction solution at higher temperatures could be reduced to substantially zero.

After the termination of the reaction, gas is fed from gas source 707 through valves 722, 723 into a washing or spectroscopic buffer tank, while the washing buffer flows through valves 726, 725, 724 onto the filter 601 for washing the filter 601 several times, to wash off the remaining primer and the residual dNTP. The liquid waste is disposed through valve 728 into liquid waste tank 703. PCR product remains on the filter 601. If unwanted matters which cannot pass through the filter 601 may possibly remain, gas may be fed through valve 728 from gas source 708, while liquid waste is disposed through valve 724 into liquid waste tank 709. As shown in FIG. 12(b), all of these motions are driven under the conditions where double strands are on the porous filter 601 in the solid phase state.

Introducing subsequently a final washing solution (serving as the spectroscopic buffer) into the PCR cell, and then inducing the inside of the PCR cell 600 into a melting state by raising the temperature, the solution flows from the PCR cell 600 toward the outlet 705 by using the gas source 708. More specifically, as shown in FIG. 12(d), a single-stranded DNA in the liquid phase is collected and then transferred into spectroscopic cell 300. In the present Example, as a washing buffer, use was made of TNE buffer (20μ 1; 10 mM Tris-HCl, 1 mM EDTA (pH 8.3), 30 mM NaCl). After introducing and measuring the sample in the spectroscopic cell 300, the sample is disposed in the liquid waste tank 704 by the flow of the washing buffer through valves 726, 727 into the cell. Consequently, the sample is disposed after such measurement while the inside of the spectroscopic cell is washed. Instead of the liquid waste tank 704, then, a fraction collector may be placed to recover the sample after the measurement.

In the above-described structure, the ratio of the numbers of the PCR cell 600 and the number of the spectroscopic cell 300 was 1:1, but attaching a plurality of PCR cells through valves to a single spectroscopic cell, the reaction products may be introduced sequentially into the spectroscopic cell for measurement.

Alternatively, by directly supplying a biological cell sample such as blood as a sample material into PCR cell 600, carrying out the extraction of a sample DNA by a known method, and subsequently carrying out the aforementioned DNA typing, the system from extraction to analysis may be made consistent. However, the overall structure of such system may possibly be more complex.

FIG. 14(a) is a side view of a structural example of the spectroscopic cell 300 employed in FIG. 13, and FIG. 14(b) is the cross sectional view.

The spectroscopic micro-cell 300 in the present Example is made of quartz glass and black quartz glass; the window of the light path is made of quartz (transparent) glass, and the remaining parts of the cell box in a rectangular parallelepiped with the upper top open are made of black quartz glass. On the upper top are internally arranged spacers of black quartz glass, with the flow gates 303 on both sides. Therefore, a sample solution holding part of a square shape, with a light path of a 10 mm length and a cross section of a 1.4 mm×1.4 mm-square shape, is formed below the spacers. A temperature sensor 301 is slightly projected toward the sample solution holding part at the central part of the spacers. As shown (inserted) with the broad arrow in the figure, the spectroscopic micro-cell 300 is placed internally inside temperature controller 302 to regulate the temperature of a sample solution.

In the present embodiment, the cell wall is made of black quartz glass with a thickness of about 1 mm, because the glass has far less reflection stray light with a relatively high thermal conductivity and a substantially great strength; for the cell material, a material with less reflection stray light and an excellent thermal conductivity is suitable. Another example is aluminum alloy coated with platinum black and TiN (titanium nitride). In the cell of the present Example, temperature sensor 301 is embedded in temperature cotoller 302 to measure the sample temperature at the central location of the light path. Therefore, the cell can regulate the temperature of samples at a high efficiency. Additionally, the cell can measure the temperature at a high precision. Furthermore, compared with general commercially-available spectroscopic cells, the cell of the present Example has such a larger surface/volume ratio of 2800 that the cell can realize the temperature increase or decrease at the rate of from 0.1° C./min to 5° C./sec.

Finally, description will now be made of an example with ethidium bromide, wherein the fluorescence from a sample DNA and the intercalating agent is detected to prepare the melting curve.

Figure 15:
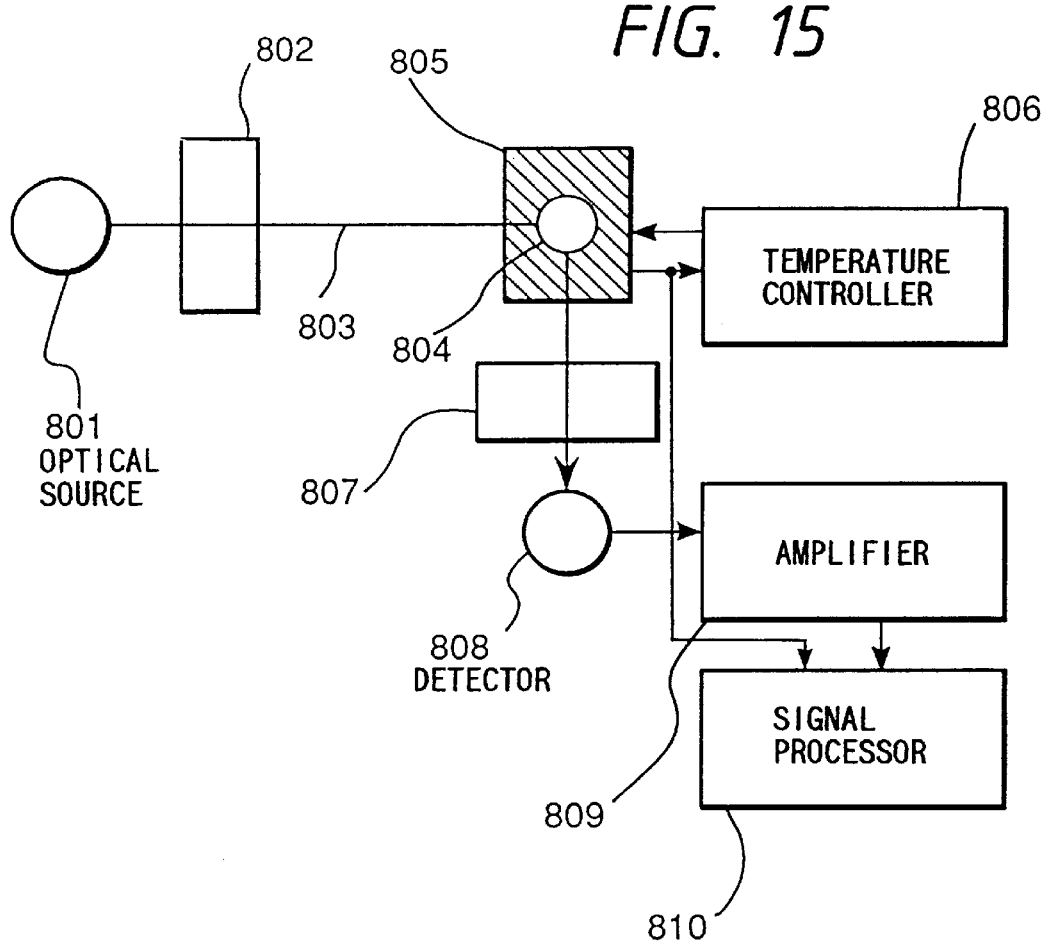
FIG. 15 is a block diagram of an example of the structure of a detector for detecting the fluorescence of the DNA and the intercalating agent.

FIG. 15 depicts the block diagram of an example of a detector structure to detect the fluorescence from the DNA and the intercalating agent. An ultra-violet ray (of a wave length of 260 nm) from light source 801 passes through a filter and optical system 802, such as a lens, to be incident into sample 804 placed in sample holder 805. Via the presence of ethidium bromide intercalated with the sample DNA, fluorescence of 590 nm is emitted, which is then collimated with the optical system 807 followed by detection with photoelectric converter 808. The signal is thereafter processed through amplifier 805 at an analytical signal processor 810. The sample holder 805 can regulate the sample temperature following the temperature profile optionally programmed with temperature controller 806. Temperature regulation can be preset optionally at a rate of temperature increase or decrease from 0.1° C./min to 2° C./sec. Temperature can be regulated within the range of −20° C. to 100° C. by an electronic heating-cooling apparatus using Peltier effect.

In the present Example, the cell may be adapted for signal processing and preventing the occurrence of bedewing on the cell surface, as described in the foregoing examples.

When determining the melting curve with the fluorescence from the intercalating agent, the fluorescence intensity decreases as the conformation of a single-stranded DNA is denatured. This is because the fluorescence emitted from the ethidium bromide intercalated with the base pairs forming the conformation is not any more emitted as the intercalation is eliminated as the conformation is denatured. The problem of reproducibility was noticed at an earlier stage, including the change of the fluorescence intensity depending on the concentration of ethidium bromide, but using the melting curve standardized on the fluorescence intensity at the lowest limit temperature, the reproducibility between samples could be secured.

Figure 16:
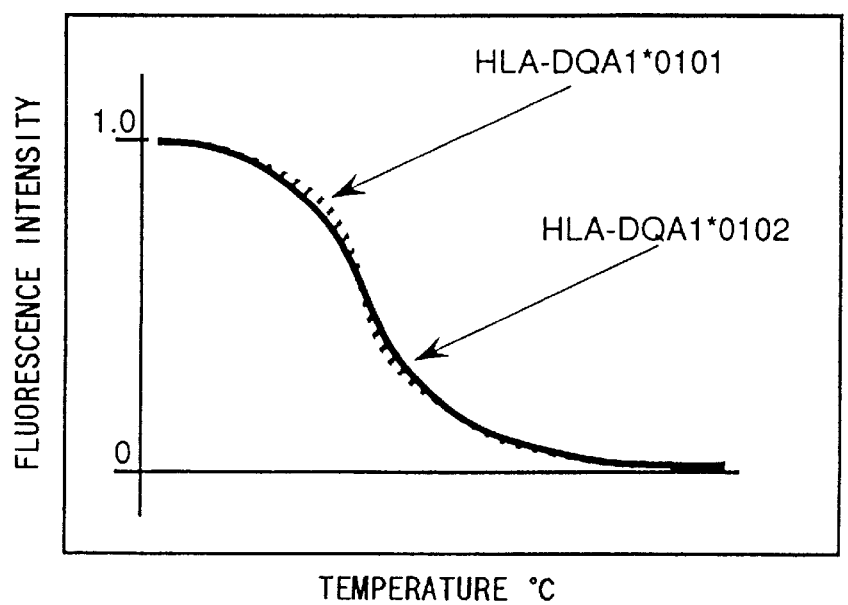
FIG. 16 is a graph of the melting curve via the fluorescence from HLA-DQA1*0101 and HLA-DQA1*0102.

FIG. 16 depicts the melting curve of HLA-DQA1*0101 and HLA-DQA1*0102 with fluorescence. In the same manner as in the case of absorbance, a single-base substitution could be identified. The data in FIG. 16 are measured at a concentration 1/50 fold that of the case of absorbance. By using fluorescence, sensitivity was improved by 10 fold to 100 fold (precision in measuring melting curve= improvement of S/N ratio).

As in the case of absorbance, signal processing is carried out on the comparison with template curves. Consequently, all samples were accurately analyzed.

In accordance with the present invention, some examples have been described insofar, but the applicable range of the present invention is not limited to these examples. A method comprising analyzing the melting curve of a single-stranded DNA, thereby producing the information of the DNA sequence, as well as a device therefor, is within the scope of the present invention.

By using the method and device in accordance with the present invention as has been mentioned insofar, DNA information at least as for clinical diagnosis and DNA tests, namely the presence or absence of a target sequence, the level thereof if present and the sequence characteristics thereof, can be obtained. The overall process from the pretreatment to the recovery of DNA information and the analysis thereof can be completed, in a short period, by the disclosed simple structure and procedures.

What is claimed is:

1. A DNA analyzer wherein said signal processing means executes the comparison of the melting curve data of the sample single-stranded DNA fragment with known melting curve data, by comparing the measured melting curve data sets with each of the data sets of known melting curves preliminarily prepared or with each of the data sets of curves prepared by linearly binding a plurality of the known melting curve data sets in combination, and determining that the data of the known melting curve with the least statistical error or the combination of the data sets with the least statistical error as the sequence characteristics of the measured single-stranded DNA fragment.

2. A DNA analyzer according to claim 1, wherein said signal processing means executes the comparison of the melting curve data of the sample single-stranded DNA fragment with known melting curve data comprises calculating the statistical error between the measured melting curve data sets and each of the data sets of known melting curves prepared or each of the data sets of the curves preliminarily prepared by linearly binding a plurality of the known melting curve data sets in combination, and representing a given number of the curve data sets in the increasing order of the statistical error as the sequence characteristics of the measured single-stranded DNA fragment.

3. A DNA analyzer according to claim 1, wherein said signal processing means presets the temperature for the denaturing condition and prepares the melting curve data as a change in the absorbance of the sample versus a change of temperature.

4. A DNA analyzer according to claim 1, wherein said signal processing means presets the temperature for the denaturing condition and prepares the melting curve data as a change in the absorbance of the sample versus a change of temperature.

5. A DNA analyzer according to claim 1, wherein said signal processing means obtains and saves data as the sequence characteristic of the single-stranded DNA fragment corresponding to the denaturing condition which alternatively changes for denaturing and forming the conformation in a time sequential manner, and prepares a hysteresis characteristics of the change in absorbance the alternative changing of denaturing condition.

6. A DNA analyzer according to claim 2, wherein said signal processing means obtains and saves data as the denaturing condition and prepares the melting curve data as a change in the absorbance of the sample versus a change of temperature.

7. A DNA analyzer according to claim 2, wherein said signal processing means obtains and saves data as the sequence characteristic of a single-stranded DNA fragment corresponding to the denaturing condition which alternatively changes for denaturing and forming the conformation in a time sequential manner, and prepares a hysteresis characteristics of the change in absorbance corresponding to the alternative changing of denaturing condition.

8. A DNA analyzer comprising:

an enzymatic reaction means for effecting selective amplification of a specific DNA region and simultaneously producing a single-stranded DNA fragment as an analytical subject;

a holding means for holding a sample solution provided by said enzymatic reaction means containing the single-stranded DNA fragment which form conformation depending on the sequence type of single-stranded DNA in the solution and the condition of the sample solution;

a spectroscopic means measuring the UV absorbance of the sample solution held in said holding means;

a denaturing means for denaturing the conformation formed by the single-stranded fragments in the sample solution held in said holding means under preset conditions; and a signal processing means for presetting the denaturing condition and for obtaining and saving signals from spectroscopic means and said denaturing means, wherein said processing means prepares the melting curve data of the single-stranded DNA fragment sample held in the holding means based on the saved signals and subsequently compares the melting curve data with the melting curve data known sequence type of single-stranded DNA fragments.

9. A DNA analyzer according to claim 8, wherein said enzymatic reaction means amplifies the single-stranded DNA fragment in a manner specific to the region by asymmetric PCR capable of replicating an excess amount of the objective single-stranded DNA fragment by setting the amount ratio of a pair of primers to be used at an uneven ratio.

10. A DNA analyzer according to claim 8, wherein said enzymatic reaction means amplifies the single-stranded DNA fragment by removing either one of a single-stranded DNA fragment which is immobilized on a support or not, from the amplified products, wherein either primer is preliminarily immobilized on the support.

11. A DNA analyzer, comprising:

a holding means for holding a sample solution containing one sequence type of single-stranded DNA fragments or plural sequence types of single-stranded DNA fragments, which form conformation depending on the sequence type of single-stranded DNA in the solution and the condition of the sample solution;

a spectroscopic means for measuring the UV absorbance of the sample solution held in said holding means;

a denaturing means for denaturing the conformation formed by the single-stranded fragments in the sample solution held in said holding means under preset conditions; and a signal processing means for presetting the denaturing conditions and for obtaining and saving signals from the spectroscopic means and said denaturing means, wherein said processing means prepares a sample melting curve data of the single-stranded DNA fragment sample held in the holding means based on the saved signals, compares the sample melting curve data with each one of the template melting curve data set of the known sequence type of the single-stranded DNA fragments provided preliminarily in said processing means, chooses one of the template melting curve data set which most closely corresponds to the sample melting curve data based on a least square method, and subsequently displays a correspondence between the sample melting curve data and the chosen one of the template melting curve data set as those melting curve data most related to each other.

12. A DNA analyzer, comprising:

a holding means for holding a sample solution containing one sequence type of single-stranded DNA fragments or plural sequence types of single-stranded DNA fragments, which form conformation depending on the sequence type of single-stranded DNA in the solution and the condition of the sample solution;

a spectroscopic means for measuring the UV absorbance of the sample solution held in said holding means;

a denaturing means for denaturing the conformation formed by the single-stranded fragments in the sample solution held in said holding means under preset conditions; and a temperature controller for presetting the denaturing conditions, and a signal processor for obtaining and saving signals from the spectroscopic means and said denaturing means, wherein said signal processor prepares a sample melting curve data of the single-stranded DNA fragment sample held in the holding means based on the saved signals, compares the sample melting curve data with each one of the template melting curve data set of the known sequence type of the single-stranded DNA fragments provided preliminarily in said processing means, chooses one of the template melting curve data set which most closely corresponds to the sample melting curve data based on a least square method, and subsequently displays a correspondence between the sample melting curve data and the chosen one of the template melting curve data set as those melting curve data most related to each other.

13. A DNA analyzer according to claim 12, wherein a temperature of said sample held in the holding means is controlled within a temperature range of about −20° C. to about 70° C.

14. A DNA analyzer according to claim 11, wherein said processing means compares the sample melting curve data with each linear combination of at least two of template melting curve data of the template melting curve data set instead of said each one of the template melting curve data set, chooses one of the linear combination of the template melting curve data which corresponds most closely to the sample melting curve data based on the least square method, and subsequently displays a correspondence between the sample melting curve data and the chosen combination of template melting curve data as are most related to each other.

15. A DNA analyzer according to claim 12, wherein said signal processor compares the sample melting curve data with each linear combination of at least two of template melting curve data of the template melting curve data set instead of said each one of the template melting curve data set, chooses one of the linear combination of the template melting curve data which corresponds most closely to the sample melting curve data based on the least square method, and subsequently displays a correspondence between the sample melting curve data and the chosen combination of template melting curve data as are most related to each other.

* * * * *